US00PP28685P3

(12) United States Plant Patent
O'Connell

(10) Patent No.: US PP28,685 P3
(45) Date of Patent: Nov. 21, 2017

(54) ***ECHEVERIA* PLANT NAMED 'DARK MOON'**

(50) Latin Name: ***Echeveria* hybrid**
Varietal Denomination: Dark Moon

(71) Applicant: Renee O'Connell, Escondido, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 48 days.

(21) Appl. No.: 14/756,706

(22) Filed: Oct. 1, 2015

(65) Prior Publication Data

US 2017/0099762 P1 Apr. 6, 2017

(51) Int. Cl.
*A01H 5/02* (2006.01)

(52) U.S. Cl.
USPC ..... Plt./373

(58) Field of Classification Search
USPC ..... Plt./263.1, 373
See application file for complete search history.

*Primary Examiner* — Keith Robinson
(74) *Attorney, Agent, or Firm* — Cassandra Bright

(57) ABSTRACT

A new and distinct *Echeveria* cultivar named 'Dark Moon' is disclosed, characterized by concentric rosettes comprised of an abundance of deep violet black leaves. The new cultivar is robust growing, as compared to other existing dark *Echeverias*, enabling increased and faster propagation of the cultivar. The new cultivar 'Dark Moon' is more resistant to disease and "shattering" (as occurs with summer stress syndrome, a disease of some *Echeverias*, particularly the dark-leaved varieties). The new variety is an *Echeveria*, part of the Crassulaceae complex that includes *Aeonium, Crassula, Graptopetalum, Pachyphytum, Sedum* and others. *Echeveria* is a popular genus, typically produced as container plants for the patio or as landscape plants, as a variety of ornamental purposes.

4 Drawing Sheets

Latin name of the genus and species: *Echeveria* hybrid.
Variety denomination: 'DARK MOON'.

BACKGROUND OF THE INVENTION

The new cultivar, *Echeveria* 'Dark Moon', is the product of a planned breeding program. The new variety originated from a cross pollination of the proprietary, unpatented, seed parent, *Echeveria* 'PB' 'PB03' with the pollen parent an unpatented, proprietary variety of *Echeveria* referred to as 'AGA'. The cross pollination was made during April 2010 in Vista, Calif., at a commercial greenhouse. The new cultivar 'Dark Moon' was discovered by the inventor, Renee O'Connell, in March 2011, in Vista, Calif. at a commercial greenhouse.

Asexual reproduction of the new cultivar 'Dark Moon' was first performed in Vista, Calif., at a commercial greenhouse, by terminal vegetative cuttings in December 2011. *Echeveria* 'Dark Moon' has since produced multiple generations and has shown that the unique features of this cultivar are stable and reproduced true to type.

SUMMARY OF THE INVENTION

The cultivar 'Dark Moon' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DARK MOON'. These characteristics in combination distinguish 'DARK MOON' as a new and distinct *Echeveria* cultivar:

1. *Echeveria* 'Dark Moon' displays compact, concentric rosettes of a deep violet-black foliage color, an unusual foliage color that is not displayed by other comparable *Echeveria* cultivars.
2. *Echeveria* 'Dark Moon' forms rosettes with slightly undulate, upturned leaves, in combination with the unusual violet-black coloration.
3. *Echeveria* 'Dark Moon' is more easily and rapidly propagated due to robust, rapid growth.
4. *Echeveria* 'Dark Moon' is more easily and rapidly propagated due to increased resistance to *Echeveria* Summer Stress Disorder that afflicts *Echeveria* 'Black Prince', *Echeveria affinis* and *Echeveria agavoides*, in particular.

PARENTAL COMPARISON

Plants of the new cultivar 'Dark Moon' can be compared to plants of the unpatented, proprietary seed parent *Echeveria* 'PB03', and are similar in most horticultural characteristics. However, plants of the new cultivar 'Dark Moon' display a dark violet-black foliage color, not displayed by *Echeveria* 'PB03'. The new cultivar 'Dark Moon' forms rosettes that are of more upright morphology than the rosettes of seed parent *Echeveria* 'PB03'.

Plants of the new cultivar 'Dark Moon' can be compared to plants of the unpatented, proprietary pollen parent *Echeveria* 'AGA', and are similar in most horticultural characteristics. However, plants of the new cultivar 'Dark Moon' exhibit more resistance to the Summer Stress Syndrome "shattering", than the pollen parent *Echeveria* 'AGA'. In addition, the new cultivar 'Dark Moon' grows more upright than the pollen parent 'AGA', resulting in less breakage of the rosette leaves during shipping, in contrast to the pollen parent 'AGA'. Further, plants of the new cultivar 'Dark Moon' are faster growing than the pollen parent 'AGA', enabling faster propagation and production in the commercial nursery.

COMMERCIAL COMPARISON

The new cultivar 'Dark Moon' can be compared to the unpatented commercial variety *Echeveria* 'Black Prince'. Plants of the *Echeveria* 'Black Prince' are similar to plants of the new cultivar 'Dark Moon' in most horticultural characteristics. However, the new cultivar 'Dark Moon' displays a more upright morphology than does *Echeveria* 'Black Prince', resulting in less leaf breakage during shipping. In addition, plants of the new cultivar 'Dark Moon' are more resistant to the Summer Stress Syndrome "shattering" than plants of *Echeveria* 'Black Prince'. Additionally, plants of the new cultivar 'Dark Moon' are faster growing than plants of *Echeveria* 'Black Prince', enhancing propagation and production times in the commercial nursery.

The new cultivar 'Dark Moon' can be compared to the unpatented commercial, unnamed *Echeveria agavoides*. Plants of *Echeveria agavoides* are similar to plants of the new cultivar 'Dark Moon' in most horticultural characteristics. However, plants of the new cultivar 'Dark Moon' display a dark violet black color not displayed by plants of *Echeveria agavoides*. In addition, the new cultivar 'Dark Moon' is more resistant to the Summer Stress Syndrome "shattering" than is *Echeveria agavoides*. Further, the new cultivar 'Dark Moon' grows much faster than *Echeveria agavoides*, resulting in much faster propagation and production times, as compared with *Echeveria agavoides*.

BRIEF DESCRIPTION OF THE PHOTOGRAPHS

The accompanying photographs in FIG. 1 through FIG. 4 illustrate in full color typical plants of 'DARK MOON' grown in a greenhouse in Vista, Calif. Age of the plant is approximately 1 year. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

DETAILED BOTANICAL DESCRIPTION

Figure 1:
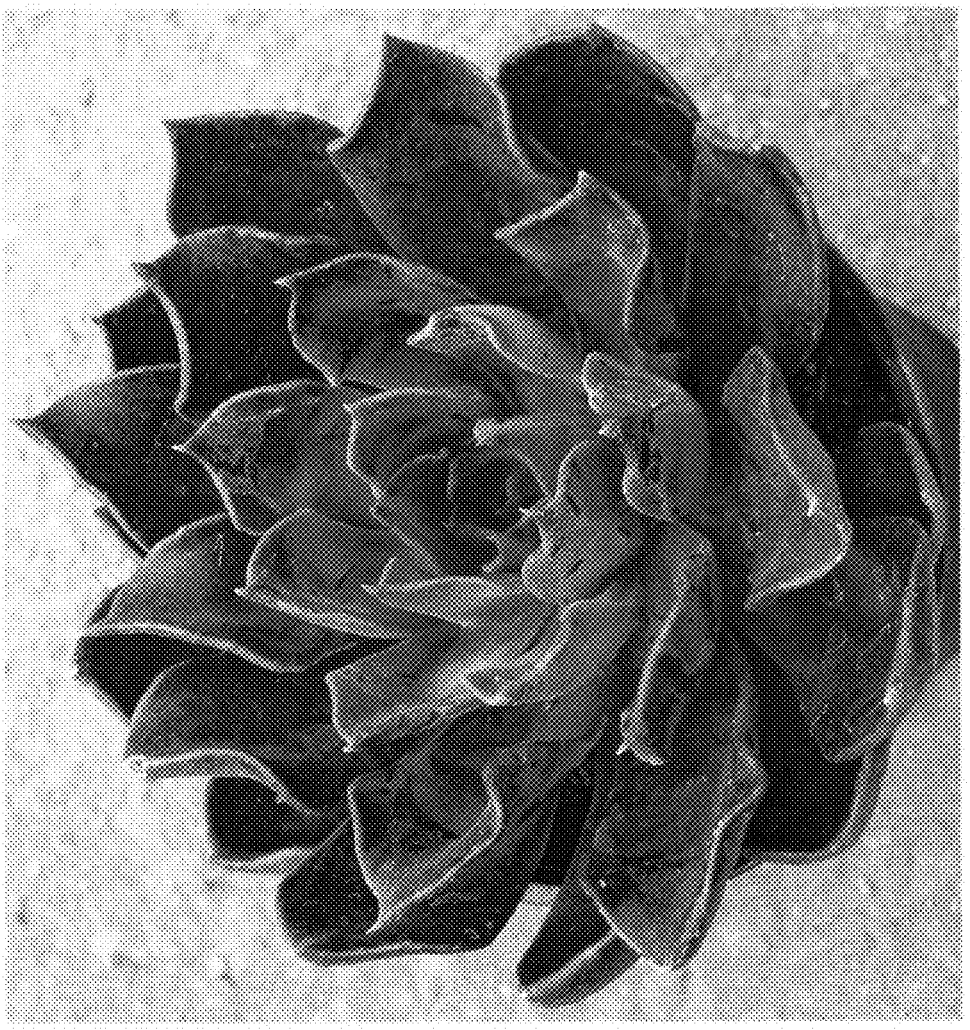
FIG. 1 illustrates in full color the top view of a rosette typical of plants of *Echeveria* 'Dark Moon' grown in a greenhouse in Vista, Calif.
Figure 2:
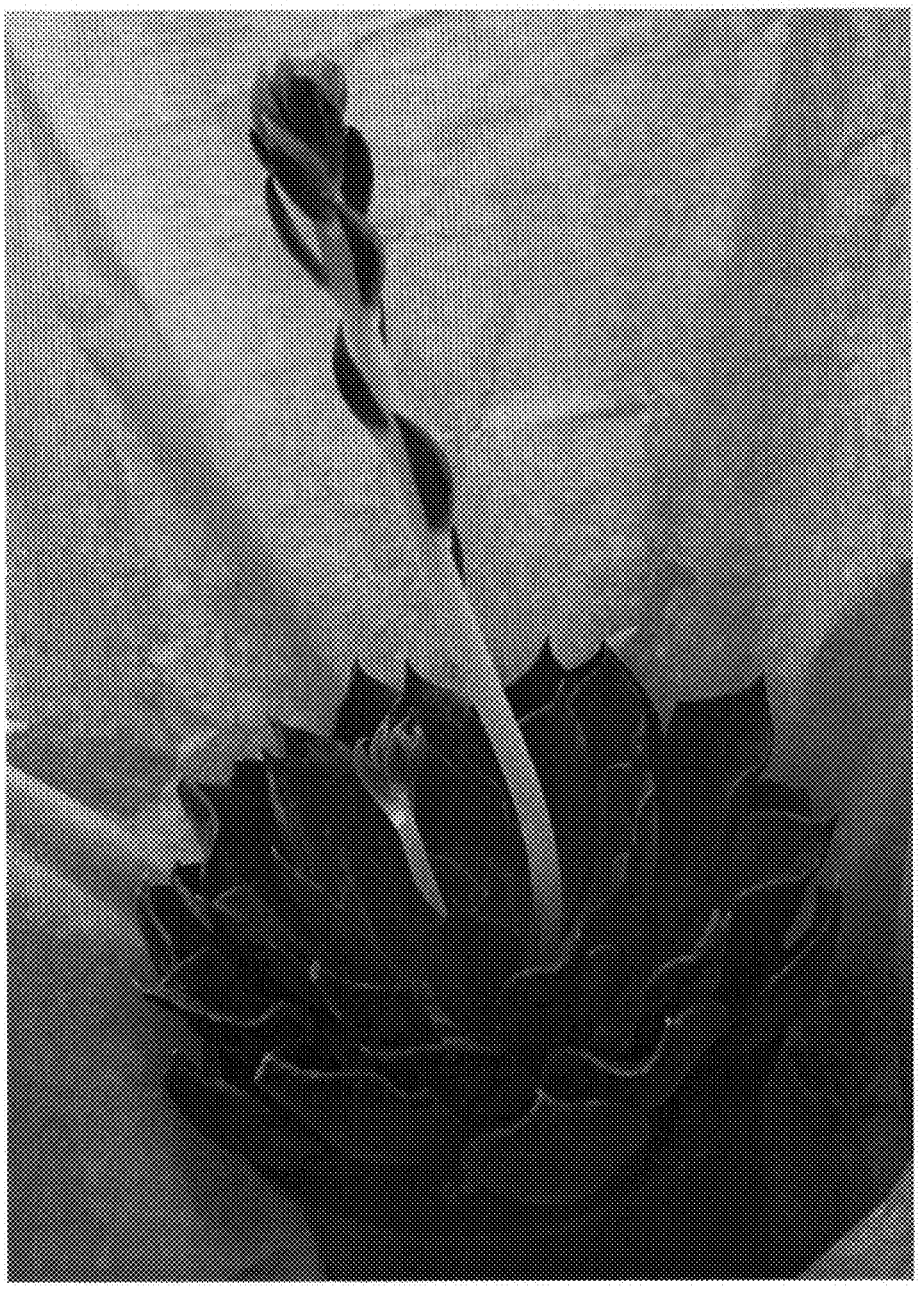
FIG. 2 illustrates in full color a rosette typical of plants of *Echeveria* 'Dark Moon' grown in a greenhouse in Vista, Calif.
Figure 3:
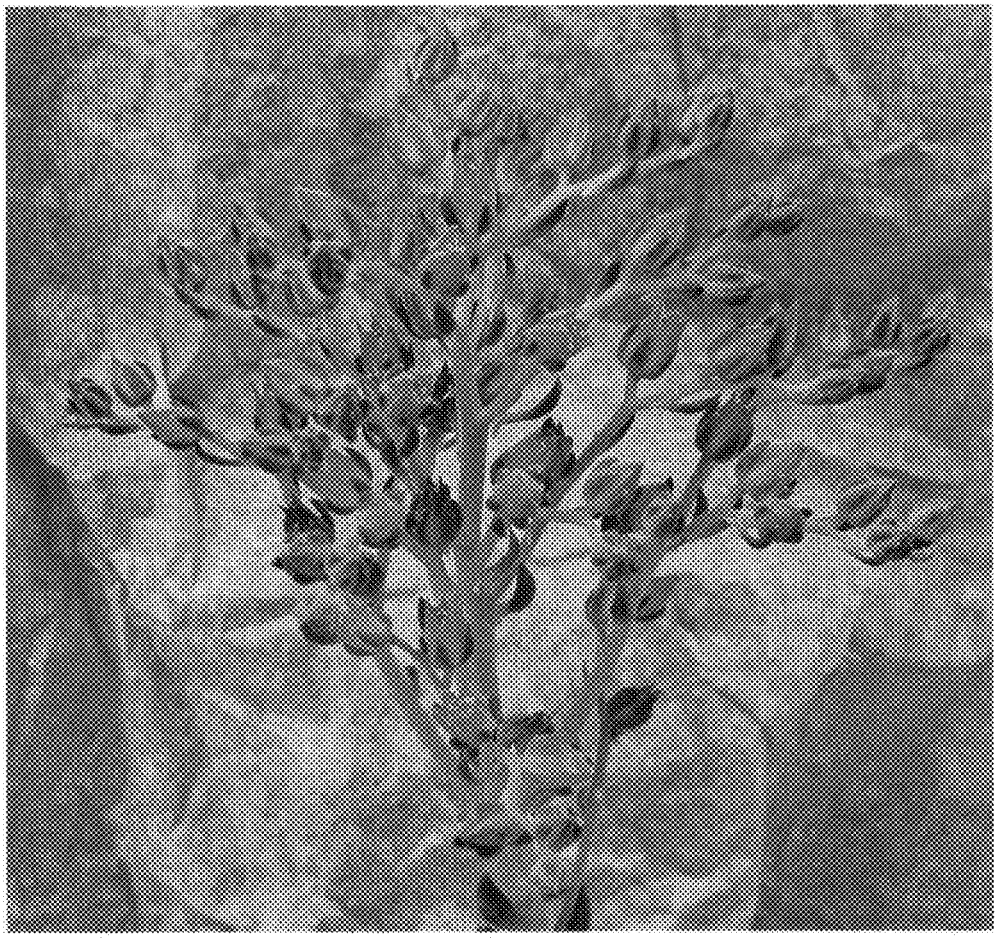
FIG. 3 illustrates in full color the inflorescence typical of plants of *Echeveria* 'Dark Moon' grown in a greenhouse in Vista, Calif.
Figure 4:
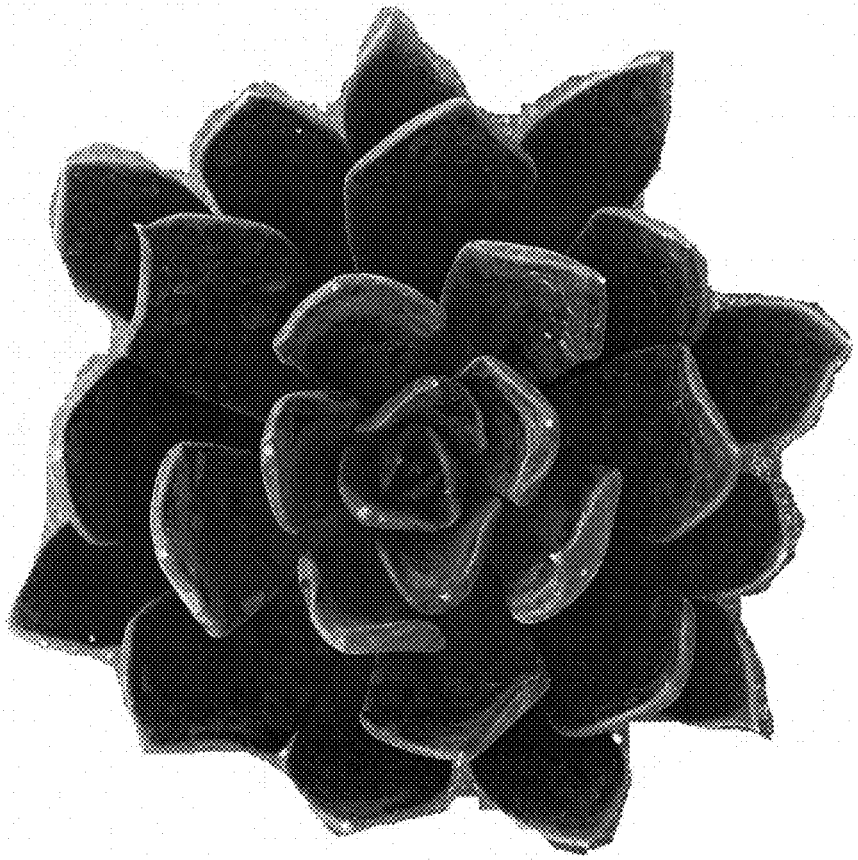
FIG. 4 illustrates in full color the rosette typical of plants of *Echeveria* 'Dark Moon' grown in a greenhouse in Vista, Calif.

In the following description, color references are made to the Pantone Process Color System Guide, Pantone CYMK, 2014, except where general terms of ordinary dictionary significance are used. The following observations and measurements describe 'Dark Moon' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'DARK MOON'.

PROPAGATION

Type of propagation typically used: Terminal vegetative cuttings.

Time to initiate roots: About 11 days at approximately 24° C.

Root description: Fibrous.

PLANT

Age of plant described: Approximately 4 months from a cutting.

Container size of the plant described: 14 cm.

Growth habit: Densely rosette plant.

Height: Approximately 11 cm to top of highest leaf Approximately 60.0 cm. to top of highest inflorescence.

Plant spread: Approximately 14.5 cm.

Growth rate: Rapid.

Branching characteristics: Not typically observed.

FOLIAGE

Leaf:

*Arrangement*.—Rosulate.

*Average length*.—Approximately 7.5 cm. Longest 10 cm.

*Average width*.—2.5 cm.

*Widest width*.—Approximately 3.3 cm.

*Width at base*.—1.1 cm.

*Shape of blade*.—Oblanceolate.

*Apex*.—Acute, mucronate.

*Base*.—Nearly elliptical.

*Margin*.—Entire.

*Texture of top surface*.—Glabrous, glaucous.

*Texture of bottom surface*.—Glabrous, glaucous.

*Quantity of leaves per plant*.—Approximately 40.

*Color*.—Young foliage upper side, towards apex: Near S 327-2 Pantone towards apex. Young foliage, upper side, apical margin: Near S 79-5 Pantone. Young foliage upper side, towards base of leaf Near S 298-7 Pantone. Young foliage, upper side, basal margin: Near S 296-7 Pantone. Young foliage, under side, towards apex of leaf : Near S 326-2 Pantone Young foliage, under side, towards base of leaf : Near S 299-6 Pantone Mature foliage upper side, towards apex of leaf Near S 329-1 Pantone. Mature foliage, upper side, towards base of leaf S 311-5 U Pantone. Mature foliage, under side, towards apex of leaf Near S 328-2 Pantone. Mature foliage, under side, towards base of leaf Near S 311-7 Pantone.

*Venation*.—There is no visual appearance of venation.

FLOWER

Natural flowering season: April, May and June.

Inflorescence type and habit: Erect, composed of several simple or bifurcate cincinni, each cincinnus with up to 6-9 flowers.

Rate of flower opening: 1 flower opens every 2-3 days.

Flower longevity on plant: 3-4 days, depending upon ambient temperatures.

Quantity of flowers: 85.

Total inflorescence size:

*Height*.—Approximately 60 cm.

*Width*.—Approximately 10 cm.

Corolla:

*Arrangement*.—Pentagonal.

*Size*.—Length: Approximately 1.2 cm. Width: Approximately 0.6 cm at widest point. Lobe Length: Approximately 0.9 cm. Lobe width: Approximately 0.75 cm.

Petals:

*Margin*.—Entire.

*Shape*.—Cylindrical.

*Apex*.—Acute.

*Base*.—Fused.

*Texture*.—Glabrous, slightly glaucous, all surfaces.

Color:

*When opening*.—Petal color, outer surface: Near S 108-1 Pantone. Petal color, outer tip: Near S 111-1 Pantone. Inner petals not visible until fully opened.

*Fully opened*.—Outer surface: Near S 107-1 Pantone. Outer surface, apex: Near S 112-1 Pantone. Inner surface: Near S 112-2 Pantone. Inner surface, apex: Near S 109-1 Pantone. Color Changes when Aging: Near S 113-3 Pantone.

Bud: (near opening):

*Shape*.—Conical.

*Length*.—Approximately 0.7 cm.

*Diameter*.—Approximately 0.45 cm.

*Color: towards apex of bud*.—Near S 112-2 Pantone.

*Color, towards base of bud*.—Near S 91-7 Pantone.

Sepals:

*Margin*.—Entire.

*Length*.—Approximately 5 mm.

*Width*.—Approximately 3 mm.

*Shape*.—Deltoid.

*Apex*.—Acute.

*Texture*.—Glabrous.

*Color*.—Outer: Near S 323-3 Pantone. Inner: Near S 323-2 Pantone.

Pedicels:

*Length*.—Approximately 1.3 cm.

*Width*.—Approximately 0.4 cm.

*Strength*.—Strong, flexible.

*Texture*.—Glabrous.

*Color*.—Near S 103-6 Pantone.

Fragrance: None detected.

REPRODUCTIVE ORGANS

Stamens: (Androecium).

*Number*.—Average 10.

*Filament length*.—Approximately 0.9 cm.

*Filament color*.—Near S 129-3 Pantone. Basal half near S 148-9 Pantone.

*Anther length*.—0.15 cm.

*Anther color*.—Near S 11-5 Pantone.

*Anther shape*.—Oblong.

*Pollen color*.—Near S 18-6 Pantone.

Pistil: (Gynoecium).

*Number*.—Average 5.

*Length*.—Approximately 0.8 cm.

*Style color*.—Near S 308-1 Pantone.

*Stigma*.—Shape: Globose. Color: Near S 308-1 Pantone. Ovary Color: Near S 18-9 Pantone.

OTHER CHARACTERISTICS

Fruits and seeds: Typical to Genus. Minute, less than 1 mm dry seeds. Colored between black and brown, too small to accurately measure with color chart.

Temperature tolerance: Tolerates temperatures from approximately −2° C. to at least 35° C.

Disease/pest resistance: More resistance to the "shattering" of Summer Stress Syndrome than other dark *Echeveria* cultivars. Neither resistance or susceptibility to other normal diseases and pests of *Echeveria* has been observed.

Drought tolerance: Tolerates at least 3 weeks of high temperatures without supplemental water, showing no serious damage to plant.

What is claimed is:

1. A new and distinct cultivar of *Echeveria* plant named 'DARK MOON' as herein illustrated and described.

* * * * *